United States Patent [19]

Harris

[11] Patent Number: 4,469,672

[45] Date of Patent: Sep. 4, 1984

[54] METHOD OF COMBINED PARENTERAL AND ORAL VACCINATION FOR SWINE DYSENTERY

[75] Inventor: Delbert L. Harris, Rothville, Mo.

[73] Assignee: Iowa State University Research Foundation, Ames, Iowa

[21] Appl. No.: 482,796

[22] Filed: Apr. 7, 1983

[51] Int. Cl.³ ............... A61K 39/02; A61K 9/14; A61K 9/18

[52] U.S. Cl. ..................... 424/23; 424/16; 424/92

[58] Field of Search ............ 424/92, 16, 35, 23, 424/357

[56] References Cited

U.S. PATENT DOCUMENTS

| | | | |
|---|---|---|---|
| 3,857,971 | 12/1974 | Abdo et al. | 424/16 |
| 4,138,498 | 2/1979 | Das | 424/93 |
| 4,152,413 | 5/1979 | Goodnow | 424/92 |
| 4,152,415 | 5/1979 | Harris et al. | 424/92 |

OTHER PUBLICATIONS

Hudson, et al., Brit. Vet. J. (1974) 130: 37.
Hudson, et al., Res. Vet. Science (1976) 21: 366.

*Primary Examiner*—Blondel Hazel

[57] ABSTRACT

The resistance of swine to dysentery infection is increased by the combined parenteral and oral administration of killed cells of *Treponema hyodysenteriae* (*T. hyo.*). A sensitizing parenteral dose of the *T. hyo.* is administered first and, after delay of a number of days, the swine are given a feed containing the killed *T. hyo.* cells adsorbed on a porous carrier. The method is particularly applicable for the protection of young, growing pigs against swine dysentery infection.

6 Claims, No Drawings

METHOD OF COMBINED PARENTERAL AND ORAL VACCINATION FOR SWINE DYSENTERY

BACKGROUND AND PRIOR ART

This invention relates to the protection of swine, especially growing pigs, against swine dysentery infection by administration of killed cells of virulent isolates of *Treponema hyodysenteriae* (*T. hyo.*). In particular, this invention relates to a method of improving the effectiveness of oral administration of *T. hyo.* cells for this purpose.

Hudson et al found that oral dosing of an attenuated strain of *T. hyodysenteriae* provided no protection against subsequent challenge. Hudson, M. J., Alexander, T. J. L., Lysons, R. J., Wellstead, P. D., *Brit. Vet. J.* (1974) 130:37. Subsequently, Hudson et al attempted to immunize pigs with live attenuated *T. hyodysenteriae* using a combination of oral dosing and parenteral inoculation. Hudson, M. J., Alexander, T. J. L., Lysons, R. J., Prescott, J. F., *Res. Vet. Science* (1976) 21:366. Oral doses were administered on three consecutive days, and after an interval of several days, intraperitoneal vaccinations were administered, which were followed after several more days by intramuscular vaccinations. The overall results of these tests were summarized as follows: "Although vaccination appeared to enhance immunity to swine dysentery, half of the vaccinated pigs developed the disease. This level of protection would be unlikely to be practical value in the field."

Attempts to successfully utilize the oral administration of *T. hyo.* cells for increasing the resistance of swine to swine dysentery have continued. U.S. Pat. No. 4,152,413 described an oral preparation in which the *T. hyo.* cells are contained within enterically coated pellets. This reference teaches that the enteric coating should be selected so that it will be resistant to dissolving in the swine's stomach while dissolving in the swine intestines. U.S. Pat. No. 4,152,415 proposes that the enteric coated vaccine of U.S. Pat. No. 4,152,415 should be used in a combined parenteral and oral immunization regimen. One or more sensitizing doses of the *T. hyo.* cells are first administered parenterally, and after a delay of at least 5 days, the enteric-coated *T. hyo.* pellets are fed on a daily basis for period of from 5 to 8 days, or longer. The combined immunization is completed before the swine contract the infection.

Subsequent work leading to the present invention has shown that the use of enteric-coated pellets of *T. hyo.* does not always give reliable results, even if combined with a sensitizing parenteral injection as described in U.S. Pat. No. 4,152,415. While the enteric coating can be designed to effectively protect the *T. hyo.* cells in the stomach, there appears to be uncertainty as to when the cells are released from the coated pellets to achieve their immunizing action in the intestines. Although not known with certainty, it is now believed that the principal immunizing action is in the small intestines, and it seems likely that the enteric coatings are not dissolved rapidly enough for full immunizing action following tranfer of the pellets from the stomach to the small intestines. Further, the preparation of enteric-coated pellets is a relatively expensive procedure, which it would be desirable to avoid, if a method could be found which provided effective oral immunization without the use of enteric coatings.

SUMMARY OF INVENTION

This invention is based in part on the discovery that uncoated expanded vermiculite can be used as a carrier for the effective oral administration of *T. hyo.* cells to prevent or reduce the severity of swine dysentery intestinal infections. Although the porous particles carrying the adsorbed cells have their pores open to the surface of the particles effective oral immunization can be obtained. This is an unexpected and surprising result with respect to swine dysentery. Vermiculite has been used as a carrier for orally administered animal vaccines, but with respect to swine dysentery it was heretofore believed that an enteric coating was necessary to protect the *T. hyo* bacteria in the stomach.

In practicing the method of this invention, it is believed to be important to use sufficiently large doses of the killed *T. hyo.* cells for both the parenteral immunizing injection and in the oral administration of the cells on the porous carrier. Further, it is believed to be important to start the oral feeding of the *T. hyo.* cells at an optimum time for the most effective immunizing action following the parenteral injection.

DETAILED DESCRIPTION

The method of this invention is applied to field-raised swine, and is particularly applicable to young, growing pigs, although it can also be applied to adult swine such as breeding sows. Young pigs to which the method is particularly applicable are referred to as feeder pigs. With such feeder pigs, the initial parenteral vaccination can be carried out either before the pigs are weaned, or subsequently, while the oral administration of the *T. hyo.* cells will be started after the pigs are weaned.

The present invention can be practiced with any virulent isolate of *T. hyo.* Attenuated or non-virulent isolates or strains are not desirable. A virulent isolate or strain is one which is capable of producing a typical swine dysentery infection. One suitable isolate is on public deposit with the American Type Culture Collection, being identified as isolate B204 and by ATCC No. 31212. Another suitable virulent isolate available from the American Type Culture Collection is identified as isolate B234 and by ATCC No. 31287. It should be understood that these isolates are representative of the class of virulent isolates or strains which can be employed.

The *T. hyo.* cells for preparation of the vaccines can be cultured according to published procedures. See U.S. Pat. No. 4,152,415 and 4,152,413, and Kinyon, et al, *Vet. Rec.* (1974) 95:219. In a modification of the published procedures, the trypticase soy broth contains bicarbonate, cysteine, dextrose, fetal bovine serum, and cholesterol. The media components are mixed under 10% $CO_2$ and 90% $N_2$ and sterlized at 250° C. Fermentation is carried out at 38° C. under constant agitation.

After the fermentation has been completed, the cells can be recovered and killed by standard procedures. Standard killing agents may be used such as formalin or methiolate. For example, a killing-concentration of formalin, such as 0.2% formalin (v/v), can be added to the fermentor or to the recovered cell slurry, if concentrated by centrification or ultrafiltration. The concentration is desirable for use of the cells in preparing the parenteral vaccine, but the cells can be used in unconcentrated form in admixture with the fermentation medium for preparation of the oral vaccine. In preparing the parenteral vaccine of *T. hyo.,* the cells may be concentrated to a suitable concentration such as $2 \times 10^{10}$ cells per milliliter (ml). Equal parts of this concentrate of killed cells can then be combined with a suitable adjuvant. For this purpose, a meat-animal acceptable adjuvant is preferred. For example, aluminum hydroxide can be used, such as a 2 to 5% aqueous solution of aluminum hydroxide (aluminum oxide basis). Other suitable adjuvants include Freund's Incomplete Adjuvant. Freund's Complete Adjuvant can be used for experimental purposes.

In the first step of the method, the swine, such as preferably growing pigs, are injected with an effective sensitizing dose of the killed $T.$ $hyo.$ cells. The vaccine may be administered by intraperitoneal injection, or other suitable parenteral procedure. In preferred embodiments of the method, a single parenteral dose is administered of at least $5 \times 10^{10}$ of the $T.$ $hyo.$ cells. Larger doses can be used to give greater assurance of effective sensitization, such as around $10 \times 10^{10}$ cells. For example, where the cell concentrate contains $2 \times 10^{10}$ cells per milliliter (ml), and is mixed in equal parts with the adjuvant, the vaccine will contain $1 \times 10^{10}$ cells/ml. The sensitizing dose may then comprise 10 ml of this vaccine, making the sensitizing dose equal approximately $10 \times 10^{10}$ cells. If desired, the sensitizing parenteral injection may be repeated, but it is preferred to use only a single injection. This provides greater efficiency and reduced cost in the commercial use of the method, and it is has been shown that a single dose of the size described is effective.

Following the sensitizing dose, after a suitable period of delay, the oral feeding of the killed $T.$ $hyo.$ cells is started. Preferably, the oral administration is started from 10 to 20 days after the parenteral administration. In an embodiment presently believed to be optimum, the oral administration is started in the period from about 12 to 16 days after the parenteral injection, such as at 14 days after the parenteral injection. Employing the method of this invention, the killed $T.$ $hyo.$ cells can be combined with the swine feed for easy, low-cost administration. At the same time, it is not necessary to employ an enteric coating to protect the orally administered cells.

With the oral administration, it is preferred to employ expanded vermiculite as a carrier for the $T.$ $hyo.$ cells. The vermiculite is in particulate form, such as in the form of a powder, which has been prepared by high temperature calcining of mineral vermiculite. In the trade, this porous, highly adsorbent particulate substance is referred to as calcined or expanded vermiculite.

In preparing the $T.$ $hyo.$ cells for oral administration, an aqueous suspension of the killed cells is applied to the porous particles of expanded vermiculite. The vermiculite will be in the form of a free-flowing mass, and the aqueous suspension of the cells will be sprayed or otherwise applied to the vermiculite particles, while they are being mixed. The spraying and mixing will be carried out so that the suspension is distributed substantially uniformly throughout the vermiculite particles, and the mixing will be continued until the suspension is substantially completely absorbed by the vermiculite. This can be assured by using sufficient vermiculite so that excess adsorption capacity is provided.

For application to the vermiculite, it is not necessary to concentrate the cells, or to carry out any other treatment than the killing of the cells. Killed cells can be used in the fermentation medium, which can provide the liquid medium in which the cells are suspended for application to the vermiculite. For example, a typical cell concentration in the fermentation medium on completion of the fermentation is about $1 \times 10^9$ cells/ml. For example, 2,500 ml of this cell-containing fermentation medium can be applied to 25 pounds of expanded vermiculite to produce sufficient oral vaccine for addition to 2,000 pounds of pig feed. The resulting feed will contain approximately $1.25 \times 10^9$ organisms per pound of feed, so that the administration of 2 pounds of the feed will provide $2.5 \times 10^9$ $T.$ $hyo.$ cells per pig per day.

In practicing the method of this invention, it is not necessary to use any other kinds of cells in combination with the $T.$ $hyo.$ cells. In the preferred embodiments, therefore, both the parenteral and the oral vaccines contain the $T.$ $hyo.$ cells as the only immunizing agent.

The method of this invention and the results obtained thereby are further illustrated by the following experimental examples.

EXAMPLE I

Cultures of T. hyodysenteriae, isolate B204, ATCC No. 31212, were prepared for experimental purposes as follows:

Tripticase peptone (5.1 grams), dipotossium phosphate (0.75 gram), phytone peptone (0.9 grams), sodium chloride (1.5 grams), dextrose (1.5 grams), sodium bicarbonate (0.6 grams) and yeast extract (3.0 grams) were dissolved in 276 ml of distilled water. The solution was mixed until all components were dissolved and 5 N HCL was used to adjust the pH to 6.85. The culture medium was boiled for 10 minutes while 10% $CO_2$ gas was bubbled into it. This was alloed to cool in a water bath and cysteine HCL (0.15 grams) and cholesteral solution (4.5 ml of a 0.2% solution) were added, still bubbling 10% $CO_2$ gas into the medium. Aliquots of 5 ml were dispensed into test tubes while bubbling 10% $CO_2$ gas into each tube. The tubes were sealed with rubber stoppers and the medium sterilized by autoclaving at 121° C. for 15 minutes. For growth of $T.$ $hyodysentariae,$ 0.5 ml of a viable culture was added to each tube. Sterile fetal bovine serum (0.2 ml) also was added to each tube prior to incubation at 38° C. for 24 hours. Inactivation was accomplished by addition of 0.2% (V/V) of 37% formaldehyde solution.

EXAMPLE II

In each of 2 experiments, 16 pigs from a herd with no history of swine dysentery (SD) were placed in isolation units at approximately 8 weeks of age and fed a 16% protein grower ration which contained no added antibiotics.

The parenterally administered vaccine was prepared from cultures produced as described in Example I. The inactivated cultures of $T.$ $hyo$ were concentrated by centrifugation. The pellets containing $T.$ $hyodysenteriae$ were resuspended in a small volume of supernatant to a concentration of approximately $2 \times 10^{10}$/ml (direct microscopic count). The concentrated suspension of antigen was emulsified equal parts with Freund's complete adjuvant. The orally administered vaccine was prepared by spraying unconcentrated, inactivated $T.$ $hyodysenteriae$ directly onto 25 pounds of expanded vermiculite contained in a rotating concrete mixer. The 25 pounds of $T.$ $hyodysenteriae$ plus vermiculite were mixed in 2000 pounds of pig feed. Each pound of feed contained approximately $1.25 \times 10^9$ organisms. After the immunization period, all pigs were challenged intragastrically with *T. hyodysenteriae* isolate B204. In experiment 1, each pig received $1 \times 10^{10}$ organisms/day on 2 successive days. In experiment 2, each pig received a single dose of $5 \times 10^{10}$ organisms.

In each experiment, 16 pigs were randomly assigned to 4 isolation units and immunized as follows. On day 1, pigs in groups I and II received an intraperitoneal injection (10ml/pig) of the parenteral vaccine. Pigs in group IV received an intraperitoneal injection (10ml/pig) of Freund's complete adjuvant emulsified equal parts with uninoculated growth medium. On day 14, groups I and III began to receive feed containing the oral vaccine. Groups I and III continued to receive the oral vaccine via the feed until the termination of the experiment. The challenge inoculum was administered on days 28 and 29 (Experiment 1) and day 28 (Experiment 2).

| | Experimental Design | | | |
|---|---|---|---|---|
| | Group No. (4 pigs/group) | | | |
| Route of Vaccine Administration | I | II | III | IV |
| Intraperitoneally | + | + | − | − |
| Orally | + | − | + | − |

Each pig was observed daily and 3 clinical parameters (general condition, feces consistency, and feces composition) were scored on a scale of 1 to 4. A rectal swab was collected from each pig 2-3 times per week and cultured for *T. hyodysenteriae*. A necropsy was performed on each pig that died during the experiments. Macroscopic lesions were recorded. The colonic mucosa was cultured for the presence of *T. hyodysenteriae* and Salmonella spp. The small intestine and mesenteric lymph nodes were also cultured for Salmonella spp. The pigs were weighed every 2 weeks and at the time of death in experiments 1 and 2. In experiment 2, the total feed consumed per group was recorded.

| Clinical Responses in Pigs Inoculated Intragestrically with *T. hyodysenteriae* | | | | |
|---|---|---|---|---|
| | No. Affected/Group | | | |
| Clinical Response | I | II | III | IV |
| Diarrhea | | | | |
| Exp. 1 | 3 | 4 | 4 | 4 |
| Exp. 2 | 4 | 4 | 4 | 4 |
| Dysentery | | | | |
| Exp. 1 | 1 | 3 | 4 | 3 |
| Exp. 2 | 4 | 4 | 3 | 4 |
| Cachexia | | | | |
| Exp. 1 | 1 | 2 | 4 | 2 |
| Exp. 2 | 1 | 3 | 1 | 4 |
| Mortality | | | | |
| Exp. 1 | 0 | 0 | 1 | 0 |
| Exp. 2 | 0 | 1 | 1 | 3 |
| Average Daily Gain | | | | |
| Exp. 1 | 1.62 | 1.42 | 1.02 | 1.29 |
| Exp. 2 | 1.40 | 1.25 | 0.88 | 0.37 |

Exp. 1 — Only 1 pig in group I had a stool characteristic of dysentery while 3 of 4 pigs were affected with dysentery in the control group. One pig died which had been immunized by the oral route only. Pigs immunized by both routes (group I) appeared better clinically, gained weight faster, and shed less *T. hyodysenteriae* in their feces as compared to either pigs vaccinated only by 1 route or pigs not vaccinated.

Exp. 2 — The ocurrence of diarrhea and dysentery was similar in all 4 groups. However, the severity of the disease was much greater in the control pigs as 3 pigs died. None of the pigs immunized by both routes died. Based on average daily gain, feed efficiency, and mortality; pigs in group I were far superior to pigs in any other group. The feces of pigs in groups I, II and III were positive for *T. hyodysenteriae* less frequently than pigs in group IV.

While expanded vermiculite is the preferred carrier for use in orally administering the *T. hyo.* cells, other equivalent carriers of similar properties can be used. The carrier should be porous, readily adsorbing the aqueous suspension of the *T. hyo.* cells. Also the carrier preferably should be non-digestable. For example, calcined diatomaceous earth is another porous silicate mineral substance which can be substituted for vermiculite. However, certain digestible or partially digestible organic materials in porous particulate form can be used to obtain some of the benefits of this invention. These include ground corn cobs, powdered milk, and wheat middlings.

I claim:

1. The method of increasing the resistance of swine to dysentery infection in which there is first parenterally administered to the swine an effective sensitizing dose of killed cells of a virulent isolate of *Treponema hyodysenteriae* (*T. hyo.*) and thereafter killed cells of a virulent isolate of *T.hyo.* are orally administered for a period of successive days before the swine contract the infection, wherein the improvement comprises carrying out said oral administration following said sensitizing parenteral administration by:

(a) applying an aqueous suspension of said killed cells of *T. hyo.* to a free-flowing mass of uncoated porous particles of vermiculite so that said suspension is distributed therethrough and adsorbed thereby;

(b) mixing said particles with a dry particulate swine feed material;

(c) feeding the resulting feed containing said *T. hyo.* adsorbed in said vermiculite particles to the swine to be protected against dysentery infection, said swine each receiving on the average at least $1 \times 10^9$ of said *T. hyo.* cells per each 24 hour day over a feeding period of at least 4 successive days.

2. The method improvement of claim 1 in which said swine are growing pigs and oral administration is started after said pigs have been weaned.

3. The method of claim 1 or claim 2 in which said swine or growing pigs each receive on the average at least $2 \times 10^9$ of said *T. hyo.* cells per each 24 hour day over a feeding period of at least ten days.

4. The method of claim 1 or claim 2 in which said swine or said growing pigs receive only one parenterally administered dose of said *T. hyo.*, said parenteral dose containing at least $5 \times 10^{10}$ of said *T. hyo.* cells, and said oral administration is started from 10 to 20 days after said parenteral administration.

5. The method of increasing the resistance of growing pigs by a sequence of parenteral and oral administrations which are carried out before the pigs contract the infection, wherein the improvement comprises the sequence of steps of:

(a) first parenterally administering to the pigs a vaccine comprising an adjuvant in admixture with a concentrate of a virulent isolate of killed cells of *Treponema hyodysenteriae* (*T. hyo.*), each animal receiving a single dose of said vaccine containing at least $5 \times 10^{10}$ of said T. hyo. cells; and (b) from 10 to 20 days after said parenteral administration beginning the oral administration of a pig feed material containing killed cells of a virulent isolate of said T. hyo. adsorbed in particles of expanded vermiculite, said vermiculite particles being uncoated with the pores thereof open to the surface of said particles, said pigs each receiving on the average at least $2 \times 10^9$ of said T. hyo. cells per each 24 hour day over a feeding period of at least 10 days.

6. The method of claim 5 in which said oral feeding is started from 12 to 16 days after said parenteral administration.

* * * * *